(12) United States Patent
Jacobson

(10) Patent No.: US 7,945,333 B2
(45) Date of Patent: May 17, 2011

(54) PROGRAMMER FOR BIOSTIMULATOR SYSTEM

(75) Inventor: Peter M. Jacobson, Chanhassen, MN (US)

(73) Assignee: Nanostim, Inc., Milpitas, CA (US)

( * ) Notice: Subject to any disclaimer, the term of this patent is extended or adjusted under 35 U.S.C. 154(b) by 679 days.

(21) Appl. No.: 11/549,605

(22) Filed: Oct. 13, 2006

(65) Prior Publication Data

US 2007/0088405 A1 Apr. 19, 2007

Related U.S. Application Data

(60) Provisional application No. 60/726,706, filed on Oct. 14, 2005, provisional application No. 60/729,671, filed on Oct. 24, 2005, provisional application No. 60/737,296, filed on Nov. 16, 2005, provisional application No. 60/739,901, filed on Nov. 26, 2005, provisional application No. 60/749,017, filed on Dec. 10, 2005, provisional application No. 60/761,531, filed on Jan. 24, 2006, provisional application No. 60/761,740, filed on Jan. 24, 2006.

(51) Int. Cl.
*A61N 1/372* (2006.01)

(52) U.S. Cl. ........... 607/59; 607/30; 607/31; 607/32; 607/60

(58) Field of Classification Search ........... 607/30–32, 607/59, 60
See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,943,936 A | 3/1976 | Rasor et al. |
| 3,946,744 A | 3/1976 | Auerbach |
| 3,952,750 A | 4/1976 | Mirowski et al. |
| 4,027,663 A | 6/1977 | Fischler et al. |

(Continued)

FOREIGN PATENT DOCUMENTS

EP 1741465 A1 1/2007

(Continued)

OTHER PUBLICATIONS

PCT International Search Report dated Apr. 8, 2008.

(Continued)

*Primary Examiner* — Niketa I Patel
*Assistant Examiner* — Hiba El-Kaissi
(74) *Attorney, Agent, or Firm* — Shay Glenn LLP

(57) ABSTRACT

A biostimulator system comprises one or more implantable devices and an external programmer configured for communicating with the implantable device or devices via bidirectional communication pathways comprising a receiving pathway that decodes information encoded on stimulation pulses generated by ones of the implantable device or devices and conducted through body tissue to the external programmer.

20 Claims, 10 Drawing Sheets

U.S. PATENT DOCUMENTS

| | | |
|---|---|---|
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A * | 3/1989 | Causey et al. ............... 607/31 |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,987,897 A * | 1/1991 | Funke ........................... 607/32 |
| 5,010,887 A | 4/1991 | Thornander |
| 5,012,806 A | 5/1991 | De Bellis |
| 5,014,700 A | 5/1991 | Alt |
| 5,014,701 A | 5/1991 | Pless et al. |
| 5,031,615 A | 7/1991 | Alt |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A * | 4/1994 | Koestner et al. ............... 607/32 |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,324,316 A | 6/1994 | Schulman et al. |
| 5,331,966 A * | 7/1994 | Bennett et al. ............... 600/508 |
| 5,333,095 A | 7/1994 | Stevenson et al. |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii et al. |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |

| | | |
|---|---|---|
| 5,669,391 A | 9/1997 | Williams |
| 5,674,259 A | 10/1997 | Gray |
| 5,676,153 A | 10/1997 | Smith et al. |
| 5,693,076 A * | 12/1997 | Kaemmerer ............... 607/59 |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A * | 4/1999 | Mann et al. ............... 607/27 |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A * | 12/2000 | Grevious ............... 607/32 |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,190,324 B1 | 2/2001 | Kieval et al. |
| 6,198,952 B1 | 3/2001 | Miesel |
| 6,201,993 B1 * | 3/2001 | Kruse et al. ............... 607/30 |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,381,492 B1 | 4/2002 | Rockwell et al. |
| 6,381,493 B1 | 4/2002 | Stadler et al. |
| 6,381,494 B1 * | 4/2002 | Gilkerson et al. ............... 607/27 |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 * | 11/2002 | Thompson et al. ............... 607/60 |
| 6,480,733 B1 | 11/2002 | Turcott |
| 6,482,154 B1 * | 11/2002 | Haubrich et al. ............... 600/300 |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 * | 6/2003 | Haupert et al. ............... 607/60 |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 * | 7/2003 | Levine ............... 607/30 |
| 6,597,948 B1 | 7/2003 | Rockwell et al. |

| | | |
|---|---|---|
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 * | 4/2006 | Goetz et al. ............. 340/870.07 |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 * | 2/2007 | Haller et al. ................. 709/219 |
| 7,187,971 B2 | 3/2007 | Sommer et al. |
| 7,200,437 B1 | 4/2007 | Nabutovsky et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,630,767 B1 | 12/2009 | Poore et al. |
| 7,634,313 B1 | 12/2009 | Kroll et al. |
| 2002/0116028 A1 | 8/2002 | Greatbatch et al. |
| 2002/0147488 A1 | 10/2002 | Doan et al. |
| 2003/0163184 A1 | 8/2003 | Schiener |
| 2004/0011366 A1 | 1/2004 | Schulman et al. |
| 2004/0143262 A1 | 7/2004 | Visram et al. |
| 2004/0147973 A1 | 7/2004 | Hauser |
| 2004/0167587 A1 * | 8/2004 | Thompson ..................... 607/60 |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 * | 7/2006 | Haubrich et al. ............... 607/60 |
| 2006/0241705 A1 | 10/2006 | Neumann et al. |
| 2006/0247750 A1 | 11/2006 | Seifert et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088418 A1 | 4/2007 | Jacobson |
| 2007/0276004 A1 | 11/2007 | Hirsch et al. |
| 2007/0293904 A1 | 12/2007 | Gelbart et al. |
| 2008/0004535 A1 | 1/2008 | Smits |
| 2008/0119911 A1 | 5/2008 | Rosero |
| 2008/0269591 A1 | 10/2008 | Halperin et al. |
| 2009/0082828 A1 | 3/2009 | Ostroff |
| 2009/0171408 A1 | 7/2009 | Solem |

FOREIGN PATENT DOCUMENTS

| | | |
|---|---|---|
| WO | WO 98/37926 A1 | 9/1998 |
| WO | WO 2006/065394 A1 | 6/2006 |
| WO | WO 2007/047681 A2 | 4/2007 |
| WO | WO 2007/059386 A2 | 5/2007 |

OTHER PUBLICATIONS

Shellock et al.; Cardiac pacemaker: in vitro assessment at 1.5 T; Am Heart J; vol. 151; pp. 436-443; 2006.

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

Beeby et al.; Micromachined silicon generator for harvesting power from vibrations; (Proceedings) PowerMEMS 2004; Kyoto, Japan; pp. 104-107; Nov. 28-30, 2004.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; 2005.

Lüchinger ; Safety aspects of cardiac pacemakers in magnetic resonance imaging; Dissertation submitted to the Swiss Federal Institute of Technology Zurich; 2002.

Nyenhuis et al.; MRI and Implanted Medical Devices: Basic Interactions with an emphasis on heating; vol. 5; No. 3; pp. 467-480; Sep. 2005.

Ostroff, Alan; U.S. Appl. No. 12/568,513 entitled "MRI Compatible Leadless Cardiac Pacemaker," Sep. 28, 2009.

Ostroff, Alan; U.S. Appl. No. 12/698,969 entitled "Leadless Cardiac Pacemaker with Secondary Fixation Capability," filed Feb. 2, 2010.

\* cited by examiner

PROGRAMMER FOR BIOSTIMULATOR SYSTEM

CROSS REFERENCE TO RELATED APPLICATIONS

This application claims the benefit of priority to and incorporates herein by reference in its entirety for all purposes, Provisional U.S. Patent Application Nos. 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Known pulse generators can include various sensors for estimating metabolic demand, to enable an increase in pacing rate proportional and appropriate for the level of exercise. The function is usually known as rate-responsive pacing. For example, an accelerometer can measure body motion and indicate activity level. A pressure transducer in the heart can sense the timing between opening and closing of various cardiac valves, or can give a measure of intracardiac pressure directly, both of which change with changing stroke volume. Stroke volume increases with increased activity level. A temperature sensor can detect changes in a patient's blood temperature, which varies based on activity level. The pacemaker can increase rate proportional to a detected increase in activity.

Pulse generator parameters are usually interrogated and modified by a programming device outside the body, via a loosely-coupled transformer with one inductance within the body and another outside, or via electromagnetic radiation with one antenna within the body and another outside.

Although more than five hundred thousand pacemakers are implanted annually, various well-known difficulties are present.

The pulse generator, when located subcutaneously, presents a bulge in the skin that patients can find unsightly or unpleasant. Patients can manipulate or "twiddle" the device. Even without persistent twiddling, subcutaneous pulse generators can exhibit erosion, extrusion, infection, and disconnection, insulation damage, or conductor breakage at the wire leads. Although sub-muscular or abdominal placement can address some of concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In many applications, such as dual-chamber pacing, multiple leads can be implanted in the same patient and sometimes in the same vessel. Abrasion between the leads for hundreds of millions of cardiac cycles can cause insulation breakdown or even conductor failure.

Data stored in memory of implanted pulse generators is typically made available to a physician or other personnel for collection and/or analysis. For example, information is sought regarding system performance and trouble-shooting relating to the device, lead system, and/or patient in an acute, clinical setting. The information is generally supplied via a telemetry capability between the external programmer and the implanted device. In addition, an external programmer can be used to adjust parameters of multi-function implantable medical devices, such as pacing rate, pulse amplitude, sensed signal gain, and pulse timing and coordination.

Typically, an external programmer used during a telemetry procedure is positioned remotely from the patient. A programming head of the programmer such as a wand or other external device, containing an antenna or coil, is connected to the remainder of the programmer via a stretchable coil cable and is positioned over the patient's implanted device site for programming or telemetry interrogation of the implanted device.

Communication between the implanted medical device and the external programmer is facilitated by receiving and transmitting circuitry included within the implanted medical device and external programmer. Bandwidth is generally kept low to minimize power consumed by the implanted medical device. Power consumption is a consideration in designing implantable medical devices since the devices are typically powered by a depletable energy source, such as a primary battery. Replacement of an implanted medical device due to battery depletion can be costly and inconvenient.

Therefore, minimization of power consumption by the implanted medical device is a design and operational consideration. To facilitate power consumption management, transmitter and receiver circuitry can be powered down when not in use but are to be awakened when desired to enable communication. Awakening can occur periodically, in which the implantable device checks for a communication signal at regular intervals. The awakening process can otherwise be achieved by using electromagnetic energy coupled to the receiving antenna or coil to facilitate the wake up function. Awakening techniques result in a complicated telemetry protocol, which generally results in longer linkup times. In addition, the awakening techniques employ a relatively large antenna or coil, which is undesirable and inconsistent with a physically compact implanted medical device.

In addition to power reduction and small size, another design criterion for implanted medical devices is accurate communication of data. Communication often occurs in environments such as hospitals and doctors' offices, which can be noisy due to the presence of other electronic and electromagnetic sources. To achieve robustness of the link, bandwidth is generally kept low, with small packet sizes. To assure that data are transmitted accurately, the antenna or coil in the implantable device is typically positioned to maximize signal strength, both transmitted and received.

SUMMARY

According to an embodiment of a biostimulator system, one or more implantable devices and an external programmer are configured for communicating with the implantable device or devices via bidirectional communication pathways comprising a receiving pathway that decodes information encoded on stimulation pulses generated by ones of the implantable device or devices and conducted through body tissue to the external programmer.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

An external programmer can be used with a system of one or more leadless cardiac pacemakers. Individual leadless cardiac pacemakers can be implanted adjacent to the inside or outside wall of a cardiac chamber. The programmer uses a minimum of two electrodes in electrical contact with the skin to communicate with each pacemaker through conduction. Information is passed from programmer to implant through a modulation technique designed to avoid stimulation of skeletal muscles. Communication from implant to programmer is performed by encoding information on the pacing pulses.

The programmer includes a user interface to display status and settings information for one or more individual implantable pacemakers, and enables the user to change programmable parameters on an individual implantable pacemaker. The programmer also can display the electrocardiogram sensed from the same two external electrodes on the skin. The programmer can perform tasks including electrocardiogram sensing, retrieving status information from implantable pacemakers, and changing configuration parameters of the implantable pacemakers simultaneously through the same set of electrodes.

Use of conducted communication of information improves over standard methods of communication in several aspects. For example, the illustrative conductive techniques enable communication without requiring a programmer head to be held undesirably close to the patient or to be held in a precise position relative to the implant site for an extended period of time. The illustrative conductive communication also enables power consumption to be reduced due to substantially lower current requirements and eliminating peak power demands currently imposed by existing inductive and radio frequency (RF) systems. Also, the conductive communication technique uses elements generally already existing in the implanted pulse generator, such as the therapeutic electrodes that function as an input-output device, enabling elimination of a coil or antenna that are conventionally used for communication and reducing complexity and component count significantly.

Figure 1A:
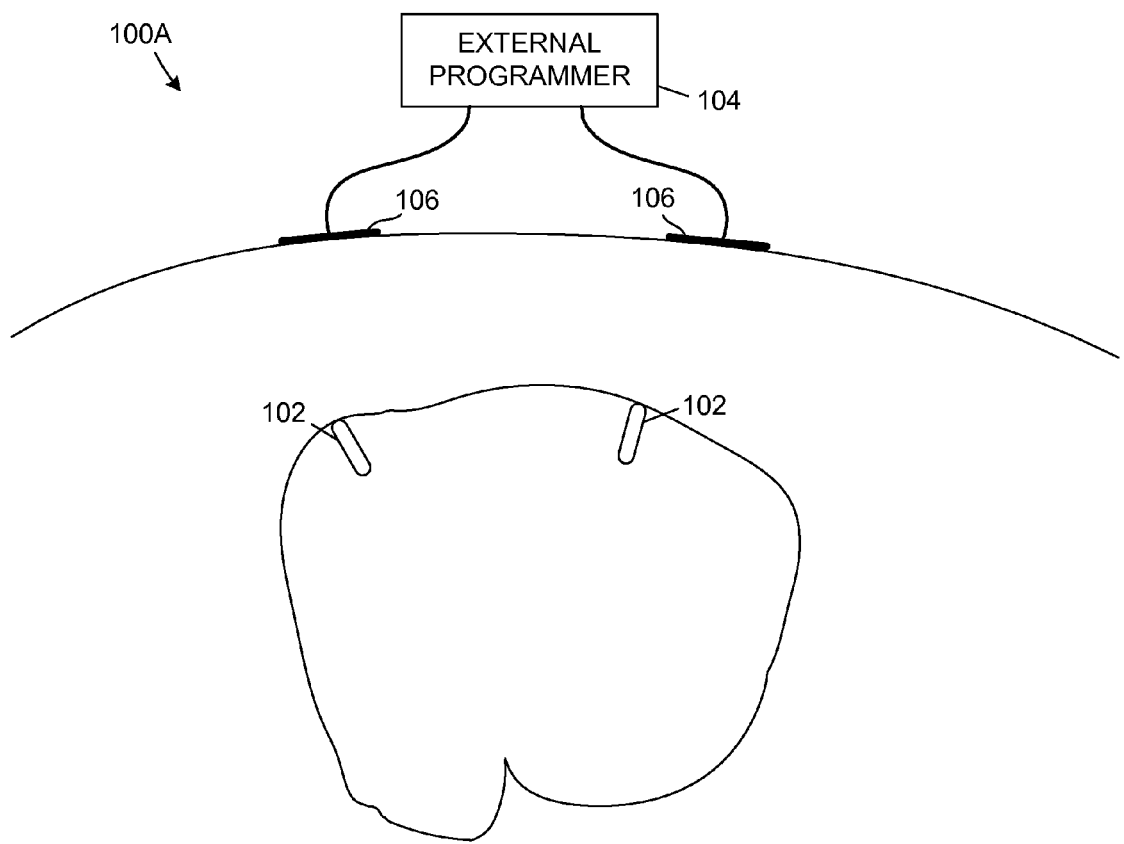
FIGS. 1A and 1B are pictorial diagrams showing embodiments of biostimulator systems comprising two leadless cardiac pacemakers secured to internal and to exterior surfaces of the heart, respectively, and an external programmer and two surface electrodes.
Figure 1B:
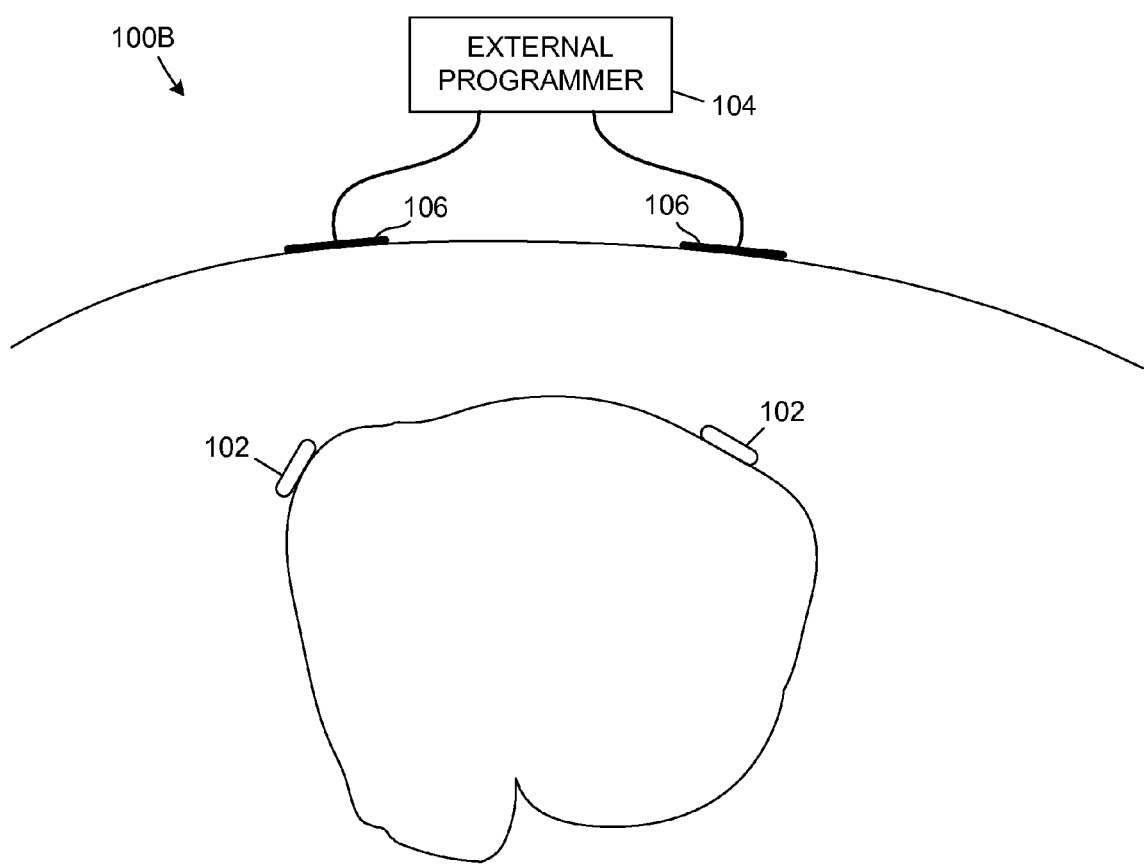

Referring to FIGS. 1A and 1B, schematic pictorial views depict embodiments of biostimulator systems 100A, 100B that communicate via conductive communication. The biostimulator systems 100A, 100B comprise one or more implantable devices 102 and an external programmer 104 configured for communicating with the one or more implantable devices 102 via bidirectional communication pathways comprising a receiving pathway that decodes information encoded on stimulation pulses generated by one or more of the implantable devices 102 and conducted through body tissue to the external programmer 104.

According to the illustrative arrangement, the bidirectional communication pathways can be configured for communication with multiple leadless cardiac pacemakers 102 via two or more electrodes 106 and conduction through body tissue.

In accordance with various biostimulator system embodiments, an external device or module 104 is connected by a communication transmission channel and has transmitting and receiving functional elements for a bidirectional exchange of information with one or more implanted medical devices 102. The communication channel includes two or more electrodes 106 which can be affixed or secured to the surface of the skin. From the point of the skin, the communication transmission channel is wireless, includes the ion medium of the intra- and extra-cellular body liquids, and enables electrolytic-galvanic coupling between the surface electrodes and the implantable modules 104.

In the biostimulator systems 100A, 100B, the bidirectional communication pathways can further comprise a transmitting pathway that passes information from the external programmer 104 to one or more of the implantable devices 102 by direct conduction through the body tissue by modulation that avoids skeletal muscle stimulation using modulated signals at a frequency in a range from approximately 10 kHz to 100 kHz.

Information transmitted from the external programmer 104 to the implanted devices 102 is conveyed by modulated signals at the approximate range of 10 kHz to 100 kHz which is a medium-high frequency. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. No restriction is imposed regarding location of electrode placement on the body because low signal attenuation enables the signal to travel throughout the body and to be received by the implanted devices 102.

In some embodiments, the bidirectional communication pathways can further comprise a receiving pathway including a low-pass filter adapted to separate the electrocardiogram from the information signals. The same surface electrodes 106 that are used to transmit the information through the communication channel may also be used to detect a patient's electrocardiogram. Electrocardiogram frequencies are generally between 1 and 100 Hz, far lower than the 10 kHz to 100 kHz range of frequencies used to transmit information through the communication transmission channel. Therefore, the electrocardiogram can be separated from the information signal by a low-pass filter and can optionally be displayed by the programmer 104. In addition to low-pass filtering, blanking techniques that are typical in processing of cardiac signals can be used when the communication channel is active to prevent noise or erroneous signals from the communication channel affecting the electrocardiogram channel.

Because a plurality of implantable devices 102 can be present, communication of information from the programmer is detected by all devices, enabling information to be sent to each implanted device without sending the same information multiple times.

In various embodiments and applications, the bidirectional communication pathways can further comprise a transmitting pathway that passes information from the programmer 104 to the one or more implantable devices 102 in a common communication event whereby information is sent to one or more target devices of the implantable devices 102 using a selected technique. For example, information specific to a single implantable device or a subset of implantable devices having a unique address can be assigned to the single implantable device or the subset of implantable devices and encoded in the information. In another technique, information can designate a specific function that is executed by a particular implantable device or a particular subset of implantable devices. The information is passed to one or more implantable devices without sending individual address information for activating execution by the particular implantable device or the particular subset of implantable devices alone. In another technique, information can designate a specific function that is executed by a particular implantable device or a particular subset of implantable devices that have programming specific to the function adapted to recognize the received information is relevant to the function.

Specifically, information that is specific to a single implanted device or a subset of devices can be sent. A unique address can be assigned to each device or subset. The address can be encoded in the information sent to the plurality of devices, and any individual device can make use only of information that matches either the address or the address of the subset to which the particular device belongs.

In another technique, if each implanted device 102 or subset of devices 102 serves a specific function, which is different from other implanted devices, then information may be passed to the specific device or subset without the additional overhead of a group or individual address. For example, the device or subset can be responsible for only a specific function. When the programmer transmits information to the entire group, but the information is relevant to only the device or subset of that group, then any devices that cannot make use of the information may ignore the information. Each device has unique programming specific to a particular function and can recognize whether received information is relevant to the function. Devices operative in conjunction with the technique can be non-generic and perform specific functions, or can be generic devices with general functionality that can be made more specific by programming. Accordingly, functionality of a device can be defined at manufacture or may be defined at implantation or thereafter. The function of each device can be defined at the time of manufacture and the devices labeled or marked such that the associated function can be known upon inspection.

In some embodiments, the one or more implantable devices 102 can comprise one or more leadless cardiac pacemakers that generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the electrodes for antenna-less and telemetry coil-less communication. For information transmitted from the implanted leadless cardiac pacemaker 102 to the external programmer 104, a communication scheme can be used in which the information is encoded on the pacing pulse. The pulse morphology is altered to contain the encoded information without altering the therapeutic benefits of the pacing pulse. The energy delivered by the pacing pulse remains essentially the same after the information is encoded. The external programmer 104 receives the pacing pulses through the associated surface electrodes 106. Encoded information is drawn from the pacing pulses and can contain state information of the implantable leadless cardiac pacemaker, such as battery voltage, lead impedance, sensed electrocardiogram amplitude, pacemaker current drain, programmed parameters, or other parameters.

The leadless cardiac pacemaker or pacemakers 102 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of a leadless cardiac pacemaker. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the leadless cardiac pacemaker. A gated segment is set sufficiently long in duration to enable accurate detection by the programmer 104, limiting the amount of information that can be transmitted during a single pacing pulse. Accordingly, a technique for communication can comprise generating stimulation pulses on stimulating electrodes of an implanted biostimulator and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information.

The three described methods of encoding information on pacing pulses can use the programmer 104 to distinguish pacing pulses from the patient's normal electrocardiogram, for example by recognition of the specific morphology of the pacing pulse compared to the R-wave generated during the cardiac cycle. For example, the external programmer 104 can be adapted to distinguish a generated cardiac pacing pulse from a natural cardiac depolarization in an electrocardiogram by performing comparative pattern recognition of a pacing pulse and an R-wave produced during a cardiac cycle.

The illustrative external programmer 104 and associated operating methods or techniques enable presentation to the user of information gathered from the implanted biostimulator or leadless cardiac pacemakers 102 using conductive communication. Some of the information to be presented may include battery voltage, lead impedance, electrocardiogram amplitude, or current drain of the device. The information can be presented in addition to other information such as parameters to be set and programmed into the leadless cardiac pacemaker. The information can be presented to a user on a display screen. Some embodiments or configurations of an external programmer 104 can include a secondary link, for example either wireless or through a cable, to another display device, such as a handheld computer or terminal. The secondary link can also include communication over a local area network or the internet for display at a remote terminal.

FIG. 1A depicts a sample configuration involving the external programmer 104 and two endocardially implanted leadless cardiac pacemakers 102. The external programmer 104 is physically connected to the skin surface via two electrodes 106, which serve three functions. First, the electrodes 106 transmit encoded information from the programmer 104 to the implanted leadless cardiac pacemakers 102 using a modulated signal at a medium frequency 10 kHz to 100 kHz. Second, the electrodes 106 receive information from individual leadless cardiac pacemakers 102 by detecting encoded information in the pacing pulses of the leadless cardiac pacemakers 102. Third, the electrodes 106 receive surface electrocardiogram for display and analysis by the programmer 104.

In FIG. 1A, the two leadless cardiac pacemakers 102 are implanted endocardially. Thus, in a biostimulator system 100A or 100B an implantable device 102 may comprise one or more leadless cardiac pacemakers that can be implanted adjacent to an inside or an outside wall of a cardiac chamber. Referring to FIG. 1B, a similar system is represented with a difference that the two leadless cardiac pacemakers 102 are implanted by affixing to the exterior surface of the heart. The electrodes 106 and programmer 104 function similarly in arrangements shown in FIGS. 1A and 1B whether the leadless cardiac pacemakers 102 are implanted endocardially or epicardially (on the external heart surface). No restriction is imposed that the leadless cardiac pacemakers are all implanted inside or all implanted outside the heart. One or more may be implanted endocardially along with others implanted on the outer surface of the heart. The functioning of the programmer 104 is substantially the same. Although two electrodes 106 are shown in FIGS. 1A and 1B, two is generally the minimum number for adequate conductive communication. More electrodes can be used, enabling an electrocardiogram (ECG) to be sensed at multiple vectors for better analysis. More than two electrodes also enable a choice of vectors for conducted communication with the leadless cardiac pacemakers, thereby maximizing the signal to noise ratio of the system. FIGS. 1A and 1B each depict two leadless cardiac pacemakers 102. One, two, or more leadless cardiac pacemakers can be implanted, depending on the number of pacemakers appropriate for effective therapy.

In various embodiments, the external programmer 104 can be configured to perform one or more operations such as electrocardiogram sensing, retrieving status information from implanted pacemakers, modifying configuration parameters of multiple implanted pacemakers simultaneously in information passed through a common electrode set, displaying electrocardiograms, displaying information received from the at least one implantable device, and others.

In various embodiments, a pacemaker 102 can manage power consumption to draw limited power from an internal battery, thereby reducing device volume. Each circuit in the pacemaker can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit can be throttled to recharge the tank capacitor at constant power from the battery. The one or more leadless cardiac pacemakers can be configured to charge the tank capacitor in preparation for stimulation pulse generation, time one or more windows between pulse generation, disable charging of the tank capacitor during the one or more timed windows, and enable a receive amplifier in the implanted biostimulator while the tank capacitor is disabled.

In some embodiments, the external programmer 104 can detect a stimulation pulse from a leadless cardiac pacemaker 102 and transmit data after a selected delay to coincide with a window that the leadless cardiac pacemaker's receiving amplifier is enabled.

The implantable devices 102 can encode and/or decode information using various techniques such as encoding the information using pacing pulse width, binary-coded notches in a pacing pulse, modulation of off-time between pacing pulses, or other suitable encoding techniques. The external programmer 104 can encode and/or decode information using on-off keying encoding and modulation techniques depicted in FIG. 3. However, any other appropriate method can be used whereby a modulated bit-stream can be generated at a medium high frequency, for example frequency-shift keying, frequency modulation, or amplitude shift keying.

Figure 2:
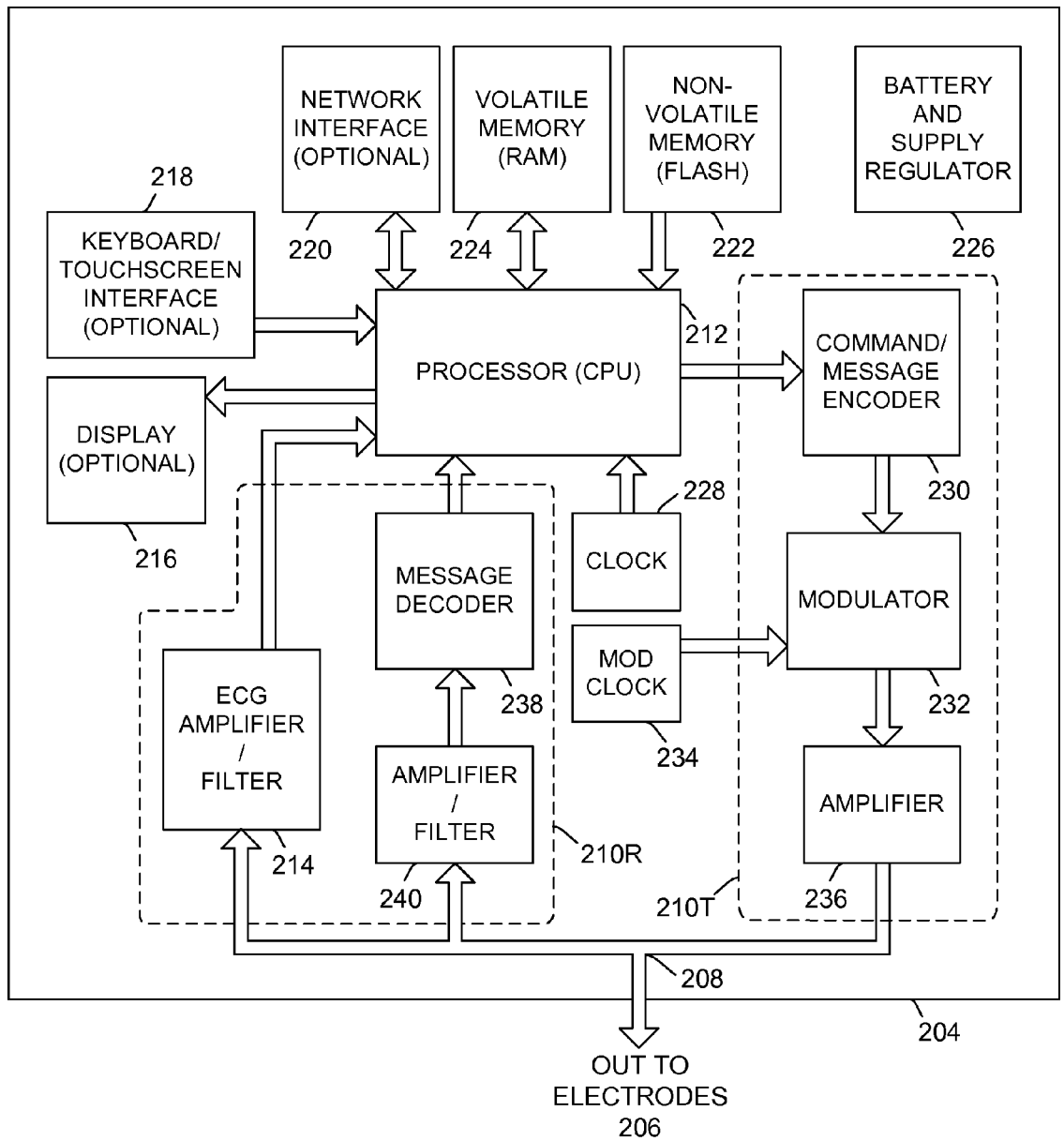
FIG. 2 is a schematic block diagram depicting an embodiment of an external programmer that can be used in a biostimulator system and adapted to communicate via conductive techniques.

Referring to FIG. 2, a schematic block diagram shows an embodiment of an external programmer 204 adapted for communicating with an implanted biostimulator system using conducted communication. The external programmer 204 comprises an interface 208 configured for coupling to at least two electrodes 206 that make electrical contact with body skin for communicating with one or more implanted biostimulators. The external programmer 204 further comprises bidirectional communication pathways 210R and 210T coupled to the interface 208 and configured for bidirectional communication with the one or more implanted biostimulators. The communication pathways comprise a receiving pathway 210R that decodes information encoded on stimulation pulses generated by the one or more implanted biostimulators and conducted through body tissue.

The bidirectional communication pathways 210R and 210T are configured for communication with one or more leadless cardiac pacemakers via the electrodes 206 and conduction through body tissue.

The external programmer 204 can have bidirectional communication pathways 210R and 210T that further comprise a transmitting pathway 210T that passes information from the programmer 204 to one or more implanted biostimulators by conduction through the body tissue using modulation that avoids skeletal muscle stimulation.

In some arrangements, the bidirectional communication pathways 210R and 210T can be further specified to comprise a transmitting pathway that passes information from the programmer 204 to the one or more implanted biostimulators by direct conduction using modulated signals at a frequency in a range from approximately 10 kHz to 100 kHz. Also in some arrangements, the two or more electrodes 206 and the bidirectional communication pathways 210R and 210T can be configured for bidirectional information signal communication and for sensing an electrocardiogram.

Also in some embodiments, the bidirectional communication pathways 210R and 210T can further comprise a transmitting pathway 210T that passes information from the programmer 204 to multiple implanted devices in a common communication event. In some embodiments or selected operating conditions, the transmitting pathway 210T can be arranged to pass information from the programmer 204 to multiple implanted devices in a common communication event whereby information specific to a single implanted device or a subset of implanted devices have a unique address assigned to the single implanted device or the subset of implanted devices and encoded in the information. The transmitting pathway 210T can also be arranged to pass information from the programmer 204 to multiple implanted devices in a common communication event whereby information designates a specific function that is executed by a particular implanted device or a particular subset of implanted devices. The information is passed to the multiple implanted devices without individual address information for activating execution by the particular implanted device or the particular subset of implanted devices alone. The transmitting pathway 210T can also be arranged, either alone or in combination with other techniques, to pass information from the programmer 204 to multiple implanted devices in a common communication event whereby information designates a specific function that is executed by a particular implanted device or a particular subset of implanted devices that comprise programming specific to the function adapted to recognize the received information is relevant to the function.

In the illustrative embodiment, the bidirectional communication pathways 210R and 210T comprise the two or more electrodes 206 forming a conductive communication path between the programmer 204 and the skin surface, and a transmitting pathway 210T. The transmitting pathway 210T comprises a processor 212, a command/message encoder 230, a modulator 232, and an amplifier 236. The processor 212 is configured to communicate information to one or more implanted leadless cardiac pacemakers. The command/message encoder 230 is coupled to the processor 212 via a parallel interface and configured to encode and serialize data into a bit stream. Information encoding can be selected from encoding techniques such as on-off keying, frequency-shift keying, frequency modulation, and amplitude shift keying. The modulator 232 is coupled to the command/message encoder 230 and receives and modulates the serialized data using a frequency in a range from approximately 10 kHz to approximately 100 kHz. The amplifier 236 is coupled to the modulator 232 and increases signal amplitude to a level suitable for robust conducted communication.

The bidirectional communication pathways 210R and 210T further comprise a receiving pathway 210R including a low-pass filter 214 adapted to separate the electrocardiogram from the information signals.

In various embodiments and arrangements, the bidirectional communication pathways 210R and 210T further comprise a receiving pathway 210R that receives information at the programmer 204 from the one or more implanted biostimulators by conduction through the body tissue. The receiving pathway 210R can decode information, for example by decoding data that is encoded by the biostimulators using pacing pulse width, using binary-coded notches in a pacing pulse, using modulation of off-time between pacing pulses, or other suitable techniques for encoding data in the biostimulators.

In the illustrative embodiment, the bidirectional communication pathways 210R and 210T couple to the two or more electrodes 206 forming a conductive communication path between the programmer 204 and the skin surface, and a receiving pathway 210R. The receiving pathway 210R comprises an electrocardiogram (ECG) amplifier/filter 214, an analog-to-digital converter (ADC) which is not shown in FIG. 2, and the processor 212. The electrocardiogram (ECG) amplifier/filter 214 includes a differential band-pass amplifier configured to select and amplify signals in a frequency range from approximately 1 Hz to approximately 100 Hz. The analog-to-digital converter (ADC) is configured to digitize the filtered and amplified signal. The processor 212 is coupled to the ADC and configured to receive and optionally display ECG data, and configured to decode information encoded into cardiac pacing pulses.

The programmer 204 may further comprise a processor 212 coupled to the bidirectional communication pathways and configured to manage communication with one or more biostimulators, for example leadless cardiac pacemakers. Leadless cardiac pacemakers can be implanted adjacent to an inside or an outside wall of a cardiac chamber as depicted in FIGS. 1A and 1B.

As depicted in FIG. 2, external electrodes 206 enable a conductive communication path between the programmer 204 and the skin surface. Electrocardiogram (ECG) signals enter an ECG amplifier/filter 214, which can include a differential band-pass amplifier. In general, an ECG signal has spectral components in a range between 1 Hz and 100 Hz. Band-pass filter poles for the ECG amplifier/filter 214 can be selected such that sufficient signal energy is passed within the 1 Hz to 100 Hz range, while filtering other signals that are not associated with cardiac activity. The ECG signal can be amplified and digitized using an analog-to-digital converter (ADC). Once digitized, the signal is passed to the processor, for example central processing unit (CPU) 212.

In some embodiments, the electrodes 206 can be implemented with more than two electrodes to enable an electrocardiogram (ECG) to be sensed at multiple vectors and further to enable selection from among the multiple vectors for conducted communication with implanted leadless cardiac pacemakers so that system signal-to-noise ratio can be improved or maximized.

The CPU 212 receives and optionally displays ECG data using a display interface 216 and can also display other data acquired from the implanted leadless cardiac pacemaker acquired through the encoded pacing pulses, such as battery voltage, lead impedance, sensed cardiac signal amplitude, or other system status information. The CPU 212 also can accept input from a user via a keyboard and/or touch-screen interface 218. Some examples of user input are selected pacing rate or pacing pulse amplitude for implanted leadless cardiac pacemakers. The CPU 212 can also communicate over a network interface 220 to other data entry or display units, such as a handheld computer or laptop/desktop unit. The network interface 220 can be cabled or wireless and can also enable communication to a local area network or the internet for greater connectivity.

The processor 212 is coupled to the bidirectional communication pathways and configured to perform one or more of various operations such as electrocardiogram sensing, retrieving status information from implanted pacemakers, modifying configuration parameters of multiple implanted pacemakers within a single or multiple cardiac cycles in information passed through a common electrode set, and other operations. A display interface 216 coupled to the processor 212 can be configured to display an electrocardiogram sensed from the electrodes 206. In some arrangements or embodiments, a secondary link 220 can be coupled to the processor 212 and configured for unidirectional or bidirectional wireless or cable transmission to and/or from a remote display and/or data-entry device to display an electrocardiogram sensed from the at least two electrodes, and/or to control the programmer and/or at least one implanted biostimulator.

The CPU 212 can execute operations based on firmware stored in non-volatile memory (Flash) 222. The non-volatile memory 222 can also be used to store parameters or values that are to be maintained when power is removed. The CPU 212 uses volatile memory or random access memory (RAM) 224 as general storage for information such as ECG data, status information, swap memory, and other data. A battery and supply regulator 226 gives a constant voltage supply to the programmer 204 during normal operation. A clock module 228 generates a system clock signal used by the CPU 212 and by interface blocks for timing.

Figure 3:
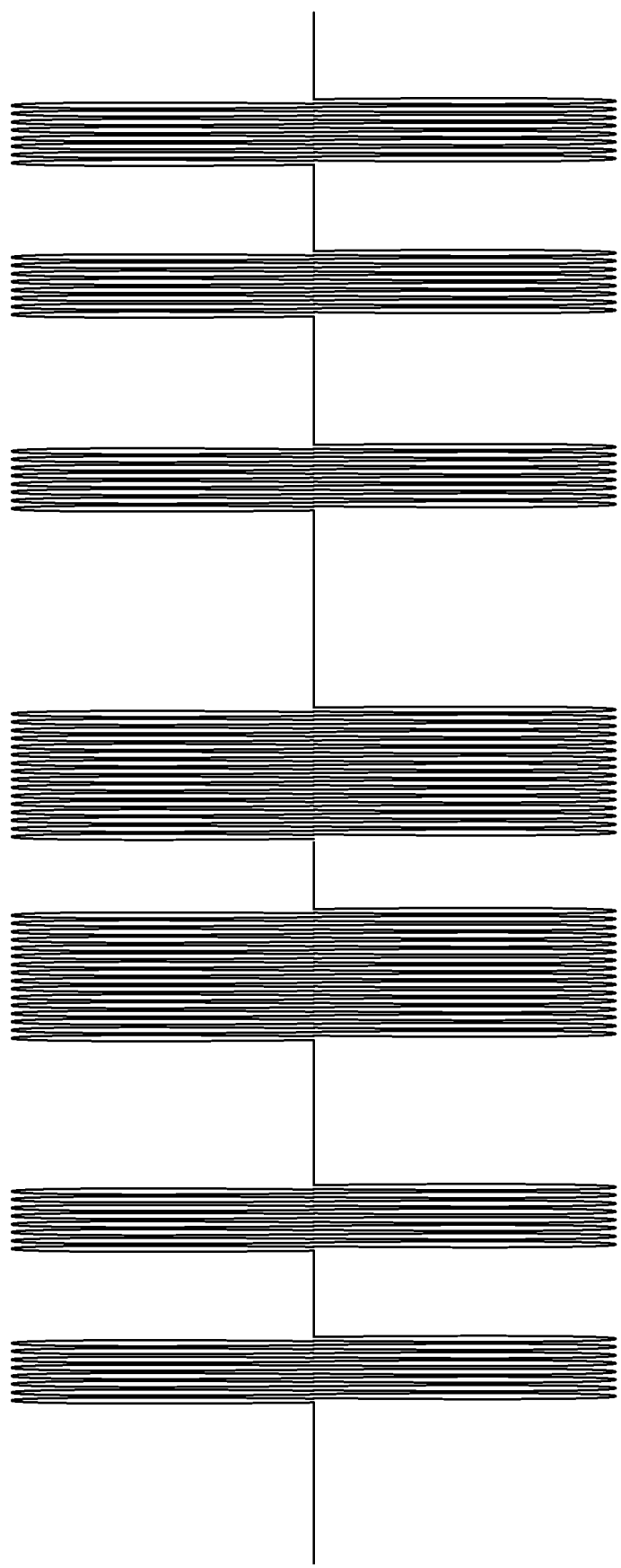
FIG. 3 is a time waveform graph showing a sample of modulated communication transmitted from an external programmer to a system of one or more leadless cardiac pacemakers.

The CPU 212, during operation to communicate information to one or more implanted leadless cardiac pacemakers, sends the information over a parallel interface to a command/message encoder 230, which serializes the data into a bit stream. Serialized data is sent to a modulator 232. The serialized bit-stream is modulated, for example using a frequency between 10 kHz and 100 kHz. An optional separate modulator clock 234 supplies a timing signal at a selected carrier frequency that may be used by the modulator 232. An amplifier 236 sets signal amplitude to a level that enables robust conducted communication. A sample of a modulated bit-steam is shown in FIG. 3 wherein logic high is shown as a medium high frequency sine wave. An encoding and modulation technique depicted in FIG. 3 is on-off keying. However, any other appropriate method whereby a modulated bit-stream can be generated at a medium high frequency may be used, for example frequency shift keying, frequency modulation, or amplitude shift keying.

Because multiple biostimulator devices can be implanted, communication of information from the programmer 204 can be detected by all devices, enabling information to be sent to each implanted device without sending the same information multiple times.

If information for communication is specific to a single implanted device or a subset of devices, a unique address can be assigned to each device or subset. The address is encoded in the information sent to the plurality of devices, and any individual device can have the option to make use of information that either matches the address or the address of the subset to which the particular device belongs.

If each implanted device or a subset of devices performs a specific function which is different from other implanted devices, then information can be passed to the specific device or subset without the additional overhead of a group or individual address. For example, when the device or subset is responsible for only a specific function. When the programmer 204 transmits information to the entire group, but the information is relevant to only the device or subset of that group, then any devices that cannot make use of the information may ignore the information as superfluous. The technique presumes that each device have unique programming specific to the associated function, and each device have capability to recognize whether or not received information is relevant to the function. Devices using the illustrative technique are not generic. The function of each device can be defined at the time of manufacture or at the time of implant or thereafter. The devices are labeled or marked such that the associated function can be known upon inspection.

To reduce the peak current for operation of the leadless cardiac pacemakers, a technique can be used in which a window or multiple windows occur between subsequent pacing pulses during which the leadless cardiac pacemaker does not charge pacing tank capacitor in preparation for the next pacing pulse. Instead the pacemaker enables an internal receiving amplifier. Because the programmer 204 can sense pacing pulses from the implanted devices, the programmer 204 can time data transmission to coincide with the predefined synchronous window or windows. A reduced peak current capability occurs because the charger and receiving amplifier, both power intensive elements, never have to be operated together. Because the data transmission is generally very short compared to the period between pacing pulses, the window technique should not significantly lower the ability of the leadless cardiac pacemaker to charge the pacing tank capacitor effectively between pacing pulses.

Referring again to FIG. 2, data acquired by the programmer 204 from a specific implanted leadless cardiac pacemaker is received at the surface electrodes 206 and passes to an amplifier/filter 240, which functions to remove noise from the incoming signal. Any filtering performed by the amplifier/filter 240 is designed to leave encoded pulses intact as much as possible. A message decoder 238 determines whether the received signal is actually a pacing pulse or another signal, such as a cardiac R-wave.

Figure 4:
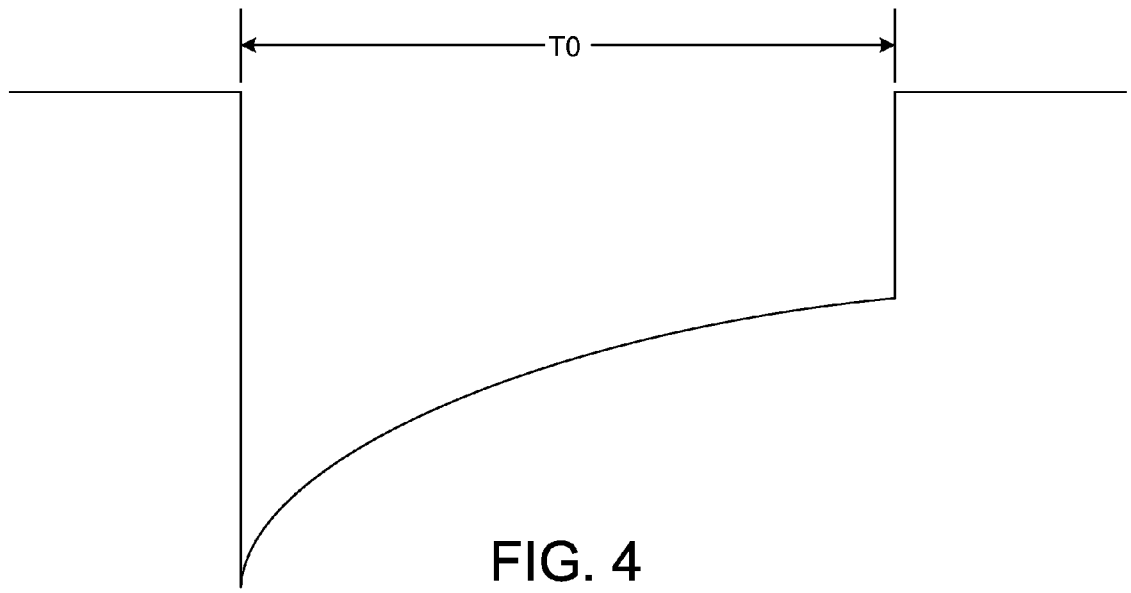
FIG. 4 is a time waveform graph illustrating a conventional pacing pulse.

FIG. 4 shows a sample pacing pulse, for example a typical output-pulse waveform for a conventional pacemaker. The approximately-exponential decay is due to discharge of a capacitor in the pacemaker through the approximately-resistive load presented by the electrodes/tissue interface and leads. Typically the generator output is capacitor-coupled to one electrode to ensure net charge balance. The pulse duration is shown as T0 and is typically 500 microseconds. When the pacemaker 102 is supplying a pacing pulse but is not sending data for communication, the waveform can resemble that shown in FIG. 4.

Figure 5:
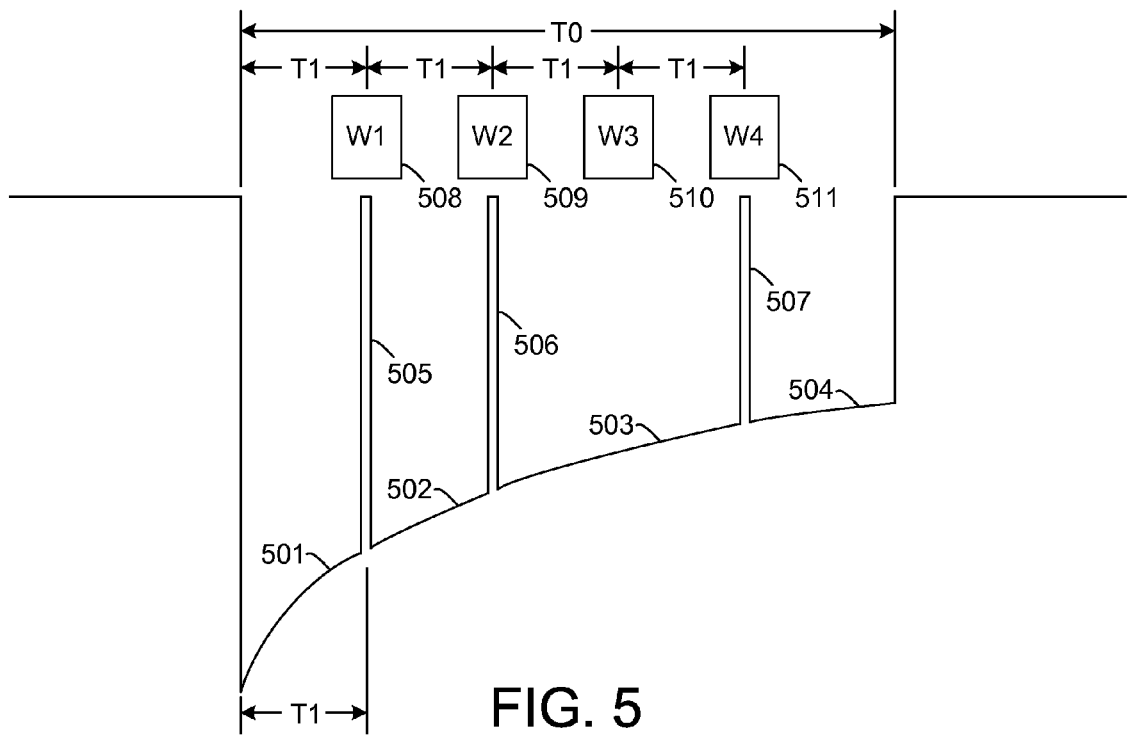
FIG. 5 is a time waveform graph depicting a pacing pulse adapted for communication as implemented for an embodiment of the illustrative pacing system.

To encode data on the pacing pulse, specific portions of the pulse are gated. Timing of the gated segments defines the specific data carried by the pacing pulse. FIG. 5 is a time waveform graph showing a sample output-pulse waveform of the illustrative pacemaker that communicates signals using conduction during a time when the pacemaker is sending data for communication and also delivering a pacing pulse.

FIG. 5 shows that the pulse generator 102 has divided the output pulse into shorter pulses 501, 502, 503, 504; separated by notches 505, 506, and 507. The pulse generator 102 times the notches 505, 506, and 507 to fall in timing windows W1, W2, and W4 designated 508, 509, and 511 respectively. Note that the pacemaker 102 does not form a notch in timing window W3 designated 510. The timing windows are each shown separated by a time T1, approximately 100 microseconds in the example.

As controlled by a processor in a leadless cardiac pacemaker 102, a pulse generator in the pacemaker selectively generates or does not generate a notch in each timing window 508, 509, 510, and 511 so that the device 102 encodes four bits of information in the pacing pulse. A similar scheme with more or fewer timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

Figure 6:
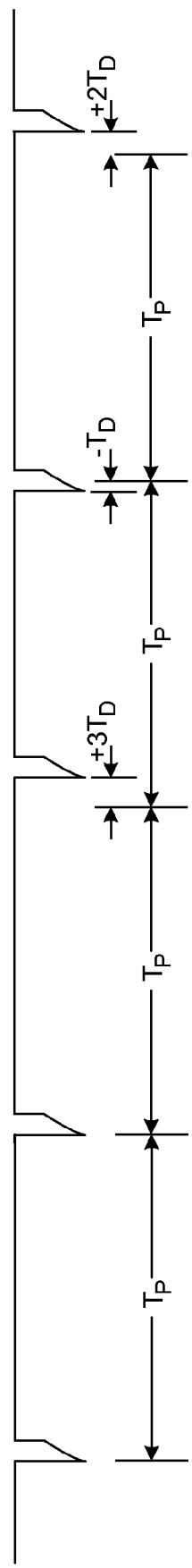
FIG. 6 is a time waveform graph showing a sample series of pacing pulses in which information is encoded by altering the interval between individual pulses.

As an alternative or in addition to using notches in the stimulation pulse, the pulses can be generated with varying off-times, specifically times between pulses during which no stimulation occurs. The variation of off-times can be small, for example less than 10 milliseconds total, and can impart information based on the difference between a specific pulse's off-time and a preprogrammed off-time based on desired heart rate. For example, the device can impart four bits of information with each pulse by defining 16 off-times centered on the preprogrammed off-time. FIG. 6 is a graph showing a sample pulse generator output which incorporates a varying off-time scheme. In the figure, time $T_p$ represents the preprogrammed pulse timing. Time $T_d$ is the delta time associated with a single bit resolution for the data sent by the pulse generator. The number of $T_d$ time increments before or after the moment specified by $T_p$ gives the specific data element transmitted. The receiver of the pulse generator's communication has advance information of the time $T_p$. The communication scheme is primarily applicable to overdrive pacing in which time $T_p$ is not dynamically changing or altered based on detected beats.

FIG. 6 shows the technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

The illustrative example avoids usage of radiofrequency (RF) communication to send pacing instructions to remote electrodes on a beat-to-beat basis to cause the remote electrodes to emit a pacing pulse. RF communication involves use of an antenna and modulation/demodulation unit in the remote electrode, which increase implant size significantly. Also, communication of pacing instructions on a beat-to-beat basis increases power requirements for the main body and the remote electrode. In contrast, the illustrative system and stimulator do not require beat-to-beat communication with any controlling main body.

The illustrative leadless pacemaker 102 includes an internal power source that can supply all energy for operations and pulse generation. In contrast, some conventional implanted pulse generators have remote pacing electrodes that receive some or all energy from an energy source through an RF induction technique, an energy transfer scheme that employs a large loop antenna on the remote electrode which increases size significantly. In addition, energy transfer with the RF induction technique is inefficient and is associated with a significant increase in battery size of the energy source. In contrast, the illustrative leadless pacemaker 102 uses an internal battery and does not require energy to be drawn from outside sources. Also in the conventional system, the energy source receives sensing information by RF communication from the remote electrodes and sends pacing instructions to the electrodes on a beat-to-beat basis in a configuration that uses an addressing scheme in which the identity of specific remote pacing electrodes is stored in the energy source memory. The conventional method can also be inefficient due to overhead for transmitting an identification number from/to a generic pacing electrode at implant and/or during sensing. The illustrative leadless pacemaker 102 avoids such overhead through a structure in which pulse generation functionality is independent within a single implantable body.

Another conventional technology uses a system of addressable remote electrodes that stimulate body tissue without requiring a main body to send commands for individual stimulations. The remote electrodes are specified to be of a size and shape suitable for injection rather than for endocardial implantation. A controller sets operating parameters and sends the parameters to remote electrodes by addressable communication, enabling the remote electrodes function relatively autonomously while incurring some overhead to controller operations. However, the remote electrodes do not sense or monitor cardiac information and rely on the main body to provide sensing functionality. In contrast, the illustrative leadless pacemaker 102 combines pacing and sensing of intrinsic cardiac activity in a single implantable body.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

In another technique, the charge current can be lowered to prevent the supply voltage from dropping below the specified level. However, lowering the charge current can create difficulty in ensuring pacing rate or pacing pulse amplitude are maintained, since the lower charge current can extend the time for the pacing tank capacitor to reach a target voltage level.

Schemes can be implemented for transmitting data from the implant to the programmer that do not significantly increase the current consumption of the pacemaker. For example, the pacemaker could transmit data continuously in a loop, with no consumption penalty.

The method of encoding data using modulation of off-time between pacing pulses is less effective if pulses are inhibited, since data can be transmitted using only pacing pulses generated by the pacemaker. When data are encoded in binary-coded notches in the pacing pulse or by varying pacing pulse width, if a therapeutic pacing pulse is inhibited, then the leadless cardiac pacemaker can still generate a non-therapeutic pulse during the refractory period of the heart after the sensed beat, although the pacing pulse has the sole purpose of transmitting data to the programmer or optionally to at least one other implanted biostimulator.

Referring to FIGS. 7A through 7E, schematic flow charts depict techniques that can be used in various embodiments of methods for communicating in an implantable biostimulator system. According to FIG. 7A, an illustrative method 700 comprises monitoring 702, at an external programmer, electrical signals conducted through body tissue to body surface electrodes and detecting 704 pulses generated by a body-implanted biostimulator. The external pacemaker decodes 706 information encoded into the generated pulse by the body-implanted biostimulator.

Figure 7A:
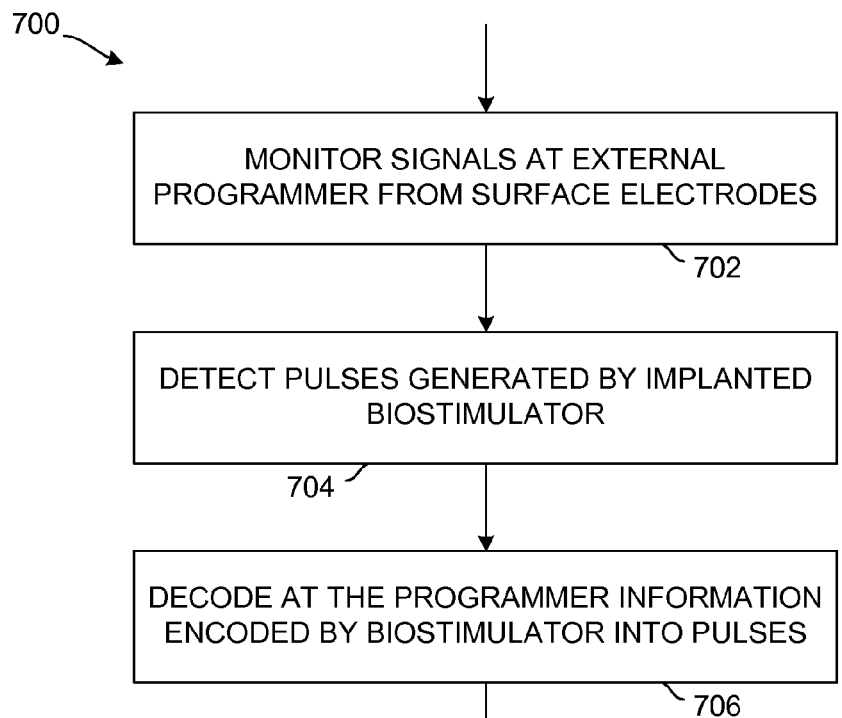
FIGS. 7A through 7E are schematic flow charts depicting techniques that can be used in various embodiments of methods for communicating in an implantable biostimulator system.
Figure 7B:
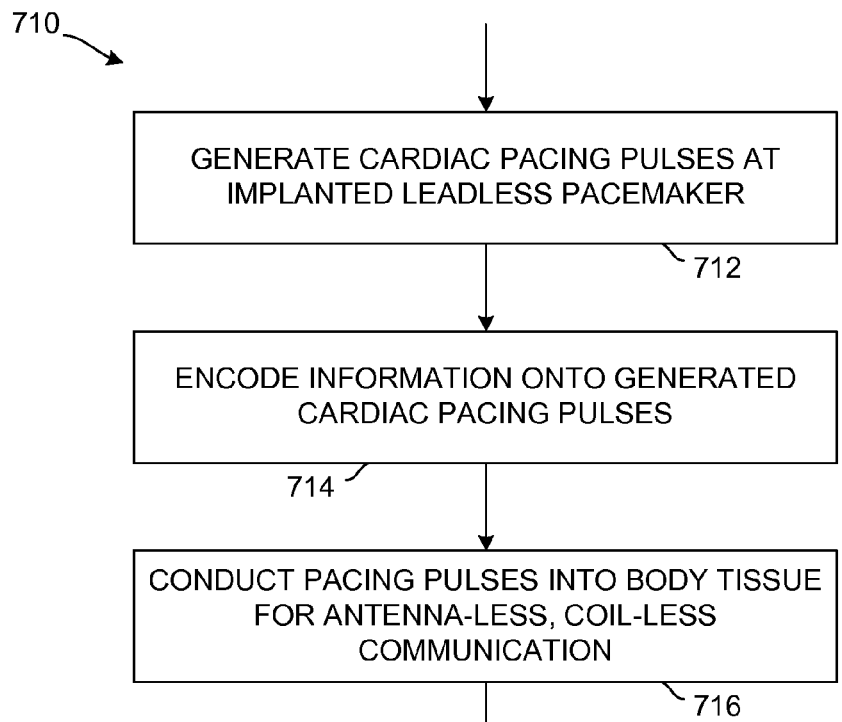

Referring to FIG. 7B, a method 710 can further comprise generating 712 cardiac pacing pulses at an implanted leadless cardiac pacemaker. Information is encoded 714 onto generated cardiac pacing pulses at the implanted leadless cardiac pacemaker by selective alteration of pacing pulse morphology that is benign to therapeutic effect and energy cost of the pacing pulse. In various embodiments, the implanted leadless cardiac pacemaker can encode the information using one or more techniques such as encoding using pacing pulse width, using binary-coded notches in a pacing pulse, and using modulation of off-time between pacing pulses. The cardiac pacing pulses are conducted 716 into body tissue via electrodes for antenna-less and telemetry coil-less communication. The information encoded onto generated cardiac pacing pulses can include pacemaker state information, battery voltage, lead impedance, sensed cardiac signal amplitude, pacemaker current drain, programmed parameters, and the like.

Figure 7C:
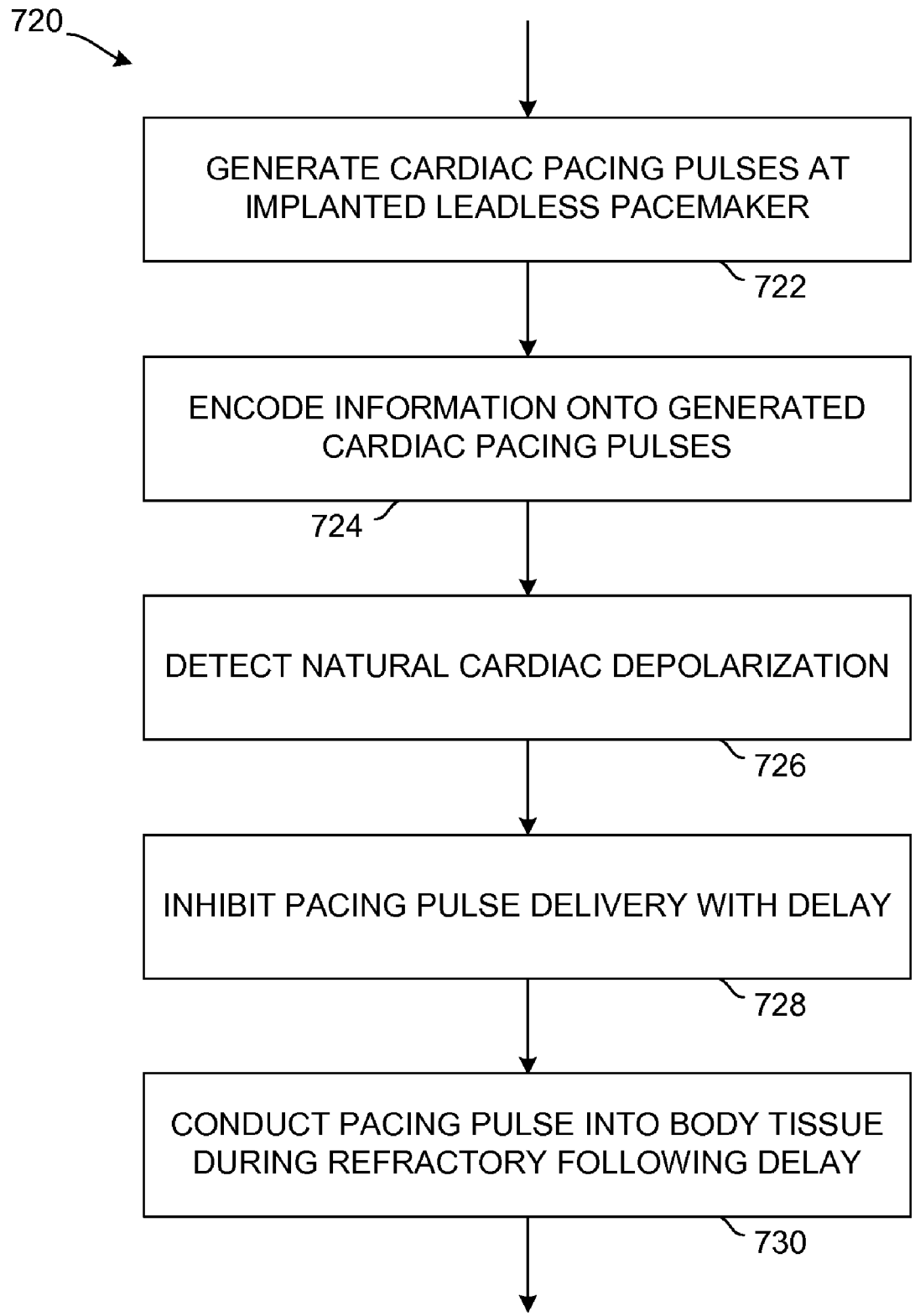

Referring to FIG. 7C, a method 720 can further comprise generating 722 cardiac pacing pulses at an implanted leadless cardiac pacemaker and encoding 724 information onto generated cardiac pacing pulses at the implanted leadless cardiac pacemaker by selective alteration of pacing pulse morphology that is benign to therapeutic effect and energy cost of the pacing pulse. The implanted leadless cardiac pacemaker detects 726 a natural cardiac depolarization and inhibits 728 cardiac pacing pulse delivery with delay for delivery during a refractory period following the natural cardiac depolarization. The cardiac pacing pulses are conducted 730 into body tissue via electrodes for antenna-less and telemetry coil-less communication.

Figure 7D:
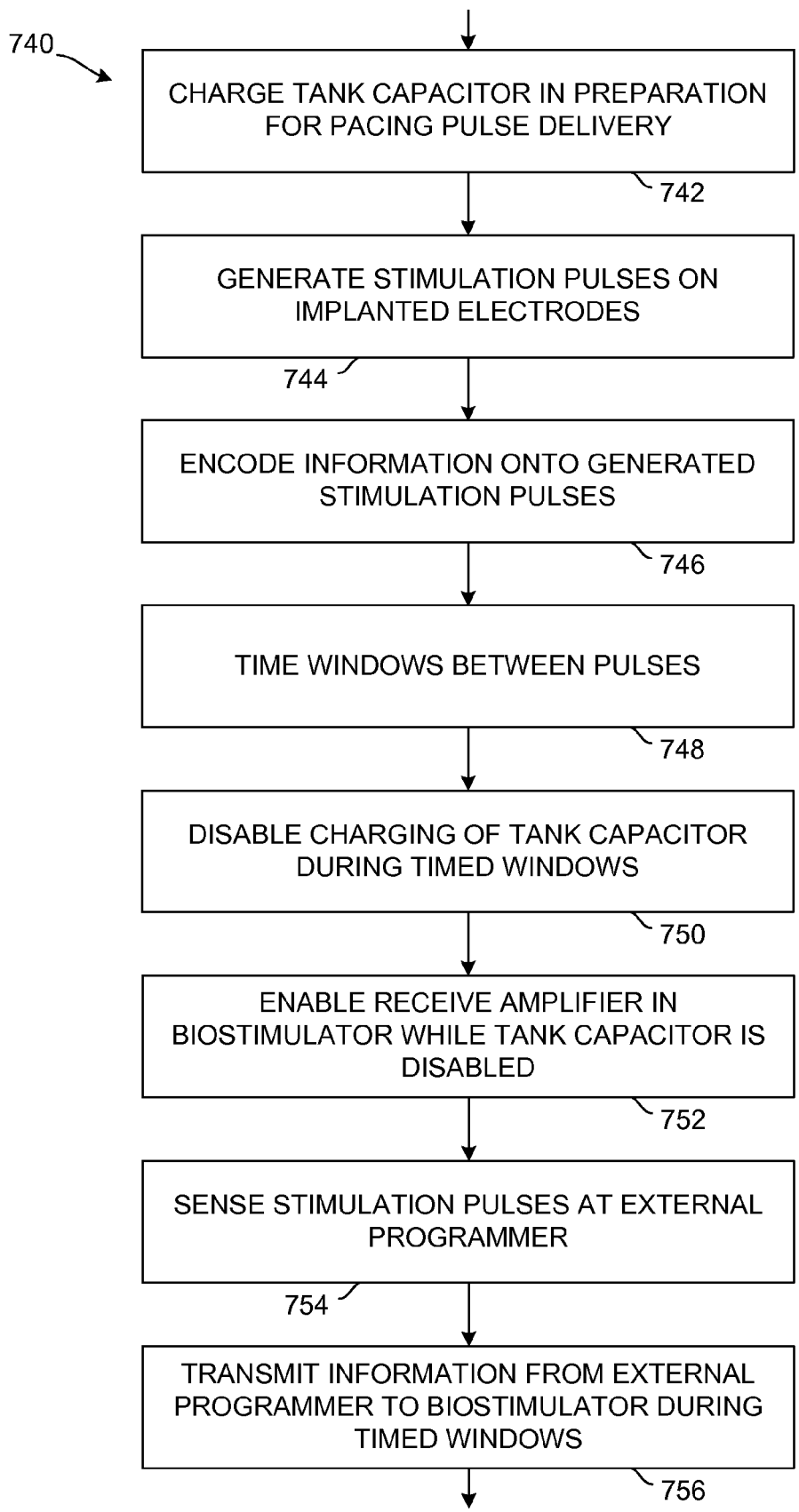

Referring to FIG. 7D, various embodiments of a method 740 can comprise charging 742 a tank capacitor in preparation for stimulation pulse generation. Stimulation pulses are generated 744 on stimulating electrodes of an implanted biostimulator and information encoded 746 onto generated stimulation pulses. One or more windows can be timed 748 between pulse generations. Charging of the tank capacitor is disabled 750 during the one or more timed windows and a receiving amplifier in the implanted biostimulator is enabled 752 while the tank capacitor is disabled. The external programmer senses 754 the stimulation pulses generated by the implanted biostimulator and transmits 756 information from the external programmer to the implanted biostimulator to coincide with the one or more timed windows. For example, the external programmer can detect a stimulation pulse from the implanted biostimulator, time a selected delay interval, and transmit data after the selected delay to coincide with a window that the implanted biostimulator's receive amplifier is enabled.

Figure 7E:
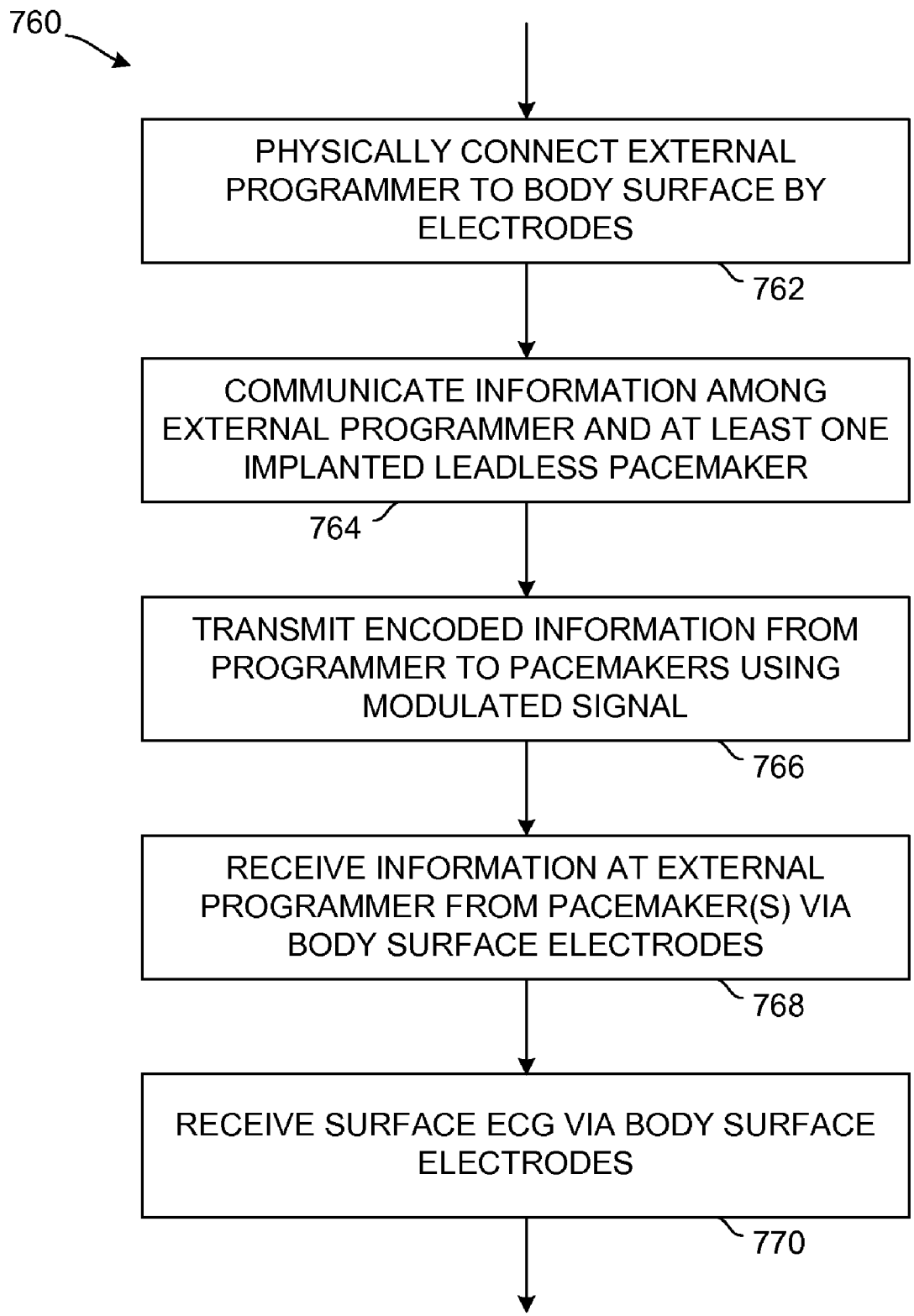

Referring to FIG. 7E, various embodiments of a method 760 can comprise physically connecting 762 the external programmer to a body surface via two or more body surface electrodes and communicating 764 information among the external programmer and one or more implanted leadless cardiac pacemakers. Encoded information is transmitted 766 from the external programmer to the implanted leadless cardiac pacemakers via the body surface electrodes using a modulated signal at a frequency in a range of approximately 10 kHz to approximately 100 kHz. The external programmer receives 768 the information via the body surface electrodes from one or more of the implanted leadless cardiac pacemakers by detecting information encoded into generated pacing pulses. The external programmer can also receive 770 a surface electrocardiogram via the body surface electrodes for display and analysis.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. An external programmer adapted for communicating with an implanted biostimulator system comprising:
    an interface configured for coupling to at least two electrodes adapted to make electrical contact with body skin for communicating with at least one implanted biostimulator;
    bidirectional communication pathways coupled to the interface configured for bidirectional communication with the at least one implanted biostimulator and comprising a receiving pathway and a processor configured to sense an electrocardiogram with the at least two electrodes and to decode information encoded on pulses generated by the at least one implanted biostimulator and conducted through body tissue and received by the receiving pathway with the at least two electrodes.

2. The programmer according to claim 1 wherein:
    the bidirectional communication pathways further comprise a transmitting pathway, the processor being further configured to pass information from the transmitting pathway and the at least two electrodes to the at least one implanted biostimulator by conduction through the body tissue by modulation that avoids skeletal muscle stimulation.

3. The programmer according to claim 1 wherein the processor is further configured to manage communication with at least one leadless cardiac pacemaker.

4. The programmer according to claim 1 wherein the processor is further configured to manage communication with at least one leadless cardiac pacemaker implanted adjacent to an inside or an outside wall of a cardiac chamber.

5. The programmer according the claim 1 wherein the processor is further configured to perform at least one operation of operations comprising retrieving status information from implanted pacemakers, and modifying configuration parameters of multiple implanted pacemakers within a single or multiple cardiac cycles in information passed through the at least two electrodes; and
    the programmer further comprising a display interface coupled to the processor and configured to display an electrocardiogram sensed from the at least two electrodes.

6. The programmer according to claim 1 wherein the processor is further configured to perform at least one operation of operations comprising retrieving status information from implanted pacemakers, and modifying configuration parameters of multiple implanted pacemakers within a single or multiple cardiac cycles in information passed through the at least two electrodes; and the programmer further comprising a secondary link coupled to the processor and configured for wireless or cable transmission to a remote display device to display an electrocardiogram sensed from the at least two electrodes.

7. The programmer according to claim 1 further comprising:
the bidirectional communication pathways configured for communication with a plurality of leadless cardiac pacemakers via the at least two electrodes and conduction through body tissue.

8. The programmer according to claim 1 further comprising:
the bidirectional communication pathways further comprising a transmitting pathway that passes information from the programmer to the at least one implanted biostimulator by direct conduction using modulated signals at a frequency in a range from approximately 10 kHz to 100 kHz.

9. The programmer according to claim 1 further comprising:
the at least two electrodes and the bidirectional communication pathways configured for bidirectional information signal communication, the bidirectional communication pathways comprising a receiving pathway including a low-pass filter adapted to separate the electrocardiogram signals from information signals.

10. The programmer according to claim 1 further comprising:
the at least two electrodes and the bidirectional communication pathways configured for bidirectional information signal communication, the receiving pathway including a low-pass filter adapted to separate electrocardiogram signals from information signals and a blanking controller configured to blank noise and unwanted signals from electrocardiogram signals when the communication channel is active.

11. The programmer according to claim 1 wherein:
the at least two electrodes comprise more than two electrodes enabling the electrocardiogram (ECG) to be sensed at multiple vectors and selection from among the multiple vectors for conducted communication with the at least one leadless cardiac pacemaker whereby system signal-to-noise ratio can be maximized.

12. The programmer according to claim 1 further comprising:
the bidirectional communication pathways further comprising a transmitting pathway that passes information from the programmer to a plurality of implanted devices in a common communication event.

13. The programmer according to claim 1 further comprising:
the bidirectional communication pathways further comprising a transmitting pathway that passes information from the programmer to a plurality of implanted devices in a common communication event whereby information specific to a single implanted device or a subset of implanted devices have a unique address assigned to the single implanted device or the subset of implanted devices and encoded in the information.

14. The programmer according to claim 1 further comprising:
the bidirectional communication pathways further comprising a transmitting pathway that passes information from the programmer to a plurality of implanted devices in a common communication event whereby information designates a specific function that is executed by a particular implanted device or a particular subset of implanted devices, the information being passed to the implanted device plurality without individual address information for activating execution by the particular implanted device or the particular subset of implanted devices alone.

15. The programmer according to claim 1 further comprising:
the bidirectional communication pathways further comprising a transmitting pathway that passes information from the programmer to a plurality of implanted devices in a common communication event whereby information designates a specific function that is executed by a particular implanted device or a particular subset of implanted devices that comprise programming specific to the function adapted to recognize the received information is relevant to the function.

16. The programmer according to claim 1 further comprising:
the at least two electrodes forming a conductive communication path between the programmer and a skin surface; and
the receiving pathway comprising:
an electrocardiogram (ECG) amplifier/filter comprising a differential band-pass amplifier configured to select and amplify signals in a frequency range from approximately 1 Hz to approximately 100 Hz;
an analog-to-digital converter (ADC) configured to digitize the filtered and amplified signal; and
the processor coupled to the ADC and configured to receive and optionally display ECG data.

17. The programmer according to claim 1 further comprising:
the at least two electrodes forming a conductive communication path between the programmer and a skin surface; and
the bidirectional communication pathways further comprising a transmitting pathway comprising:
a processor configured to communicate information to at least one implanted leadless cardiac pacemaker;
a command/message encoder coupled to the processor and configured to encode and serialize data into a bit stream, the encoding being selected from a group of encoding techniques consisting of on-off keying, frequency-shift keying, frequency modulation, and amplitude shift keying;
a modulator coupled to the command/message encoder that receives and modulates the serialized data using a frequency in a range from approximately 10 kHz to approximately 100 kHz; and
an amplifier coupled to the modulator that increases signal amplitude to a level suitable for robust conducted communication.

18. The programmer according to claim 1 further comprising:
the receiving pathway that decodes information encoded using pulse width.

19. The programmer according to claim 1 further comprising:
the receiving pathway configured to decode information encoded using binary-coded notches in a pulse.

20. The programmer according to claim 1 further comprising:
the receiving pathway configured to decode information encoded using modulation of off-time between pulses.

* * * * *